United States Patent
Meersseman et al.

(10) Patent No.: US 10,829,758 B2
(45) Date of Patent: Nov. 10, 2020

(54) AUTOMATABLE METHOD FOR NUCLEIC ACID ISOLATION

(71) Applicant: Biocartis NV, Mechelen (BE)

(72) Inventors: Geert Meersseman, Brussels (BE); Klaas DeCanniere, Ottenburg (BE)

(73) Assignee: BIOCARTIS, NV, Mechelen (BE)

(*) Notice: Subject to any disclaimer, the term of this patent is extended or adjusted under 35 U.S.C. 154(b) by 96 days.

(21) Appl. No.: 15/570,947

(22) PCT Filed: Jun. 9, 2016

(86) PCT No.: PCT/EP2016/063150
§ 371 (c)(1),
(2) Date: Oct. 31, 2017

(87) PCT Pub. No.: WO2016/198519
PCT Pub. Date: Dec. 15, 2016

(65) Prior Publication Data
US 2018/0291367 A1      Oct. 11, 2018

(30) Foreign Application Priority Data

Jun. 9, 2015   (EP) ..................................... 15171261

(51) Int. Cl.
*C12N 15/10* (2006.01)
*C12Q 1/68* (2018.01)
*C12Q 1/686* (2018.01)

(52) U.S. Cl.
CPC ......... *C12N 15/1006* (2013.01); *C12Q 1/686* (2013.01)

(58) Field of Classification Search
None
See application file for complete search history.

(56) References Cited

U.S. PATENT DOCUMENTS

| 6,383,393 B1 * | 5/2002 | Colpan | C12N 15/101 |
| | | | 210/198.2 |
| 2003/0152974 A1 | 8/2003 | Gauche | |
| 2014/0051844 A1 * | 2/2014 | Forman | C12Q 1/6806 |
| | | | 536/24.5 |

FOREIGN PATENT DOCUMENTS

| EP | 1690938 A1 | 8/2006 |
| EP | 2128169 A1 | 12/2009 |
| EP | 2345719 A1 | 7/2011 |
| JP | 2005137298 | 6/2005 |
| JP | 2007325562 | 12/2007 |
| JP | 2008529509 | 8/2008 |
| WO | 0171732 | 9/2001 |
| WO | 2004108925 A1 | 12/2004 |
| WO | 2010145843 A1 | 12/2010 |
| WO | 0029563 A1 | 7/2011 |
| WO | 2013024072 A1 | 2/2013 |
| WO | 2014144174 | 9/2014 |
| WO | WO-2014144174 A1 * | 9/2014 ........... C12Q 1/6806 |

OTHER PUBLICATIONS

European Examination Report for EP3307907 dated Jan. 17, 2019.
European Patent Office, European Office Action for application 16732490, dated Sep. 26, 2019.
Soya, Y. Development of Molecular Testing Using Novel Gene Analyzer, GENECUBE System. Biological sample analysis, 2013, vol. 36, No. 4, p. 310-315. English Abstract.
Janku, F., et al. "BRAF mutation testing with a rapid, fully integrated molecular diagnostics system." Oncotarget 6.29 (2015): 26886.
Japan Patent Office, Office Action for application 2017-563581, dated Aug. 6, 2019, with English Translation.
International Search Report for PCT/EP2016/063150 dated Sep. 13, 2016.
Written Opinion for PCT/EP2016/063150 dated Sep. 13, 2016.

* cited by examiner

*Primary Examiner* — Teresa E Strzelecka
*Assistant Examiner* — Olayinka A Oyeyemi
(74) *Attorney, Agent, or Firm* — Quarles & Brady LLP

(57) ABSTRACT

The present invention relates to a highly automatable method for isolation and/or purification of nucleic acids from a biological sample, which is particularly suitable for nucleic acids-shorter than 250 bp and can be performed without a proteolytic pre-digestion step in an automated system, preferably a cartridge-based system. In a further aspect, the present invention also provides automated nucleic acid detection methods based on said isolation and/or purification method, as well as buffers and kits to be used in performing said methods.

16 Claims, 4 Drawing Sheets

Fig. 6

AUTOMATABLE METHOD FOR NUCLEIC ACID ISOLATION

CROSS-REFERENCE TO RELATED PATENT APPLICATIONS

The present application is the U.S. national phase application of International Application No. PCT/EP2016/063150, filed on Jun. 9, 2016, which application claims the benefit of priority to European Patent Application No. 15171261.9, filed on Jun. 9, 2015, the contents of which are incorporated herein by reference in their entireties.

FIELD OF THE INVENTION

The present invention relates to a highly automatable method for isolation and/or purification of nucleic acids from a biological sample, which is particularly suitable for nucleic acids shorter than 250 bp and can be performed without a proteolytic pre-digestion step in an automated system, preferably a cartridge-based system. In a further aspect, the present invention also provides automated nucleic acid detection methods based on said isolation and/or purification method, as well as buffers and kits to be used in performing said methods.

BACKGROUND TO THE INVENTION

Isolation of nucleic acids is currently most often performed based on one of two different principles. The first and earlier one employs a one-step extraction procedure whereby a buffer containing a chaotropic agent and an organic extractant (usually phenol and/or chloroform) is added to a biological sample. As a result, the thus obtained mixture separates into two phases: the aqueous phase retaining the nucleic acids and the organic phase retaining the undesired leftover which can be discarded. Important disadvantages of this one-step extraction procedure are, firstly, the use of toxic and harmful substances such as phenol and/or chloroform, and, secondly, the possible contamination of the nucleic-acid retaining aqueous phase with other water-soluble substances. These substances can be removed by performing additional purification steps which, however, are time-consuming.

The second principle is based on selected adsorption of nucleic acids onto solid support materials such as silicon dioxide, for example as disclosed in EP0389063, which provides for a nucleic acid isolation procedure practically free from the above-listed disadvantages. In brief, the procedure involves lysis, if necessary, of the nucleic acid containing starting material, followed by contacting said material with the support material under defined conditions to enable binding of the nucleic acids to the support material. Optionally, washing and elution steps can be performed using suitable solutions or buffers.

A well-known variation of the above procedure called the "Boom protocol" (Boom et al., *J. Clin. Microbiol.* 1990, 28(3)) is disclosed in EP0819696. The Boom protocol involves isolating nucleic acids from a nucleic acid containing starting material by incubating said starting material with a chaotropic buffer and a DNA-binding solid phase. The chaotropic buffer affects, if necessary, both the lysis of the starting material and the binding of the nucleic acids to the solid phase.

The Boom protocol and many known in the prior art variations thereof are mostly suitable for the extraction and purification of nucleic acids larger than 1 kilobase (kb), like bacterial plasmids typically having a length between 3-10 kb. This can presumably be attributed to the fact that adsorption of short-chain nucleic acids (i.e. of less than 250 nucleotides (nt) in length) to the solid support material is inferior to that of longer nucleic acids. Nevertheless, for certain applications, isolation of short-chain nucleic acids or concentrating them over long-chain nucleic acids is desirable, for example for the isolation and detection of short-chain fragmented nucleic acids circulating in body fluids, such as the so called cell-free DNA (cfDNA) found in blood of cancer patients or during pregnancy.

In order to preferably purify, concentrate, or separate short-chain nucleic acids over long-chain nucleic acids, various protocols have been described. One of them is described in WO2009146776 (EP2285816) that teaches isolation and/or purification of nucleic acids with a length of <1000 nt by binding them to a siliceous support material in the presence of at least one chaotropic compound in a concentration of ≥2 M and ≤3.5 M and isopropanol in a concentration of ≥15% (v/v) and ≤32% (v/v). The procedure however suffers from a drawback that the afore-mentioned conditions cause rapid precipitation of proteins present in biological samples, which without an appropriate pre-treatment can substantially impair adsorption of nucleic acids to the support material and also cause clogging of such support materials as membranes or purification columns. Therefore, the isolation protocol as disclosed in EP2285816 has to preceded by a proteolytic treatment involving at least a 15-30 minute incubation with a protease (Proteinase K) at a temperature of above 50-60° C., which is essential for the success of the procedure. The fact that the nucleic acid-containing starting material has to be first pre-digested before being contacted with the support material in the presence of the chaotrope and isopropanol, not only causes the protocol to be more time-consuming and labour-intensive, which interferes with its effective implementation on automatic systems, but importantly also increases the chances of nucleic acid degradation, in particular of short-chain nucleic acids but also and especially of different types of RNAs.

Therefore, it is an object of the present invention to address the above-stated drawbacks by providing a simple and rapid method for isolating and/or purifying nucleic acids, which does not require a proteolytic pre-treatment and is suitable for automation. Importantly, the method of the present invention is particularly advantageous for isolating short-chain nucleic acids having a length of <250 bp from liquid biopsies but can also serve to isolate various intracellular and extracellular nucleic acid species such as viral nucleic acids or microRNAs.

SUMMARY OF THE INVENTION

The present invention is defined in the appended independent claims. Preferred embodiments are defined in the dependent claims. In particular, the present invention concerns a method for isolation and/or purification of nucleic acids from a nucleic acid-containing starting material, the method comprising the steps of:
  (a) binding the nucleic acids to a nucleic acid binding support material by contacting the nucleic acid-containing starting material with the nucleic acid binding support in the presence of at least one chaotropic compound and at least one alcohol; and (b) optionally eluting the bound nucleic acids from the nucleic acid binding support material with an elution solution, such as pure water or an elution buffer e.g. TE buffer;

the method characterized in that
(i) the alcohol is an alcohol having 4 or 5 carbon atoms and is present in step a) in a concentration between 17% (v/v) and 60% (v/v), and in that
(ii) the at least one chaotropic compound is present in step a) in a concentration between 1.5 M and 5 M.

State-of-the-art methods for isolation of nucleic acids derived from the Boom protocol are based on the adsorption of nucleic acids to a solid phase in the presence ethanol or isopropanol. These known methods require proteolytic pre-digestion of biological samples in order to prevent substantial protein precipitation that happensin said conditions, even if a chaotropic agent is present at a high concentration. By employing a 4 or 5 carbon atom alcohol, the present invention substantially sidesteps the persisting precipitation problem and thus also makes the use of the standard proteolytic pre-digestion step redundant. Thus, in a particularly advantageous embodiment, the present invention provides a nucleic acid isolation and/or purification method, wherein no protease is added to step a), or wherein no incubation with a protease, or any equivalent step, is performed before subjecting the nucleic acid-containing starting material to the step a). Thanks to these features, the method of the present invention is particularly suitable for being performed in an automated manner.

In a further aspect, the present invention also provides an automated diagnostic method for detecting nucleic acids on an automated system, the method comprising the steps of:
a) providing a nucleic acid-containing starting material into an automated system;
b) isolating and/or purifying nucleic acids in said automated system, according to the isolation and/or purification method in accordance with the above embodiments;
c) performing a PCR in said automated system on target nucleic acids isolated and/or purified in step (b); and
d) detecting the target nucleic acids generated in the PCR in step (c), preferably also on said automated system.

Next, the present invention further provides an aqueous extraction buffer for isolation and/or purification nucleic acids said buffer comprising:
(i) an alcohol having 4 or 5 carbon atoms, in a concentration between 20% (v/v) and 65% (v/v), preferably between 35% (v/v) and 60% (v/v), most preferably between 40% (v/v) and 50% (v/v) and
(ii) at least one chaotropic compound in a concentration between 3.3 M and 6.7 M, preferably between 3.5 M and 5.5 M, most preferably between 3.7 M and 4.5 M.

In another preferred embodiment, the present invention also provides a kit for isolation and/or purification of nucleic acids said kit comprising at least the aqueous extraction buffer as described above. In a preferred embodiment, such kit can be in a form of a cartridge wherein the aqueous extraction buffer according to the invention is provided inside of said cartridge.

Lastly, also provided are the uses of the afore-listed nucleic acid isolation and/or purification method, automated diagnostic method, aqueous extraction buffer, and the kit according to the invention in any of the following:
isolation and/or purification of extracellular nucleic acids;
isolation and/or purification of short-chain nucleic acids having a length of <250 nt;
isolation and/or purification of viral nucleic acids, diagnosis of infections, as well as pathological or physiological conditions.

Definitions

The term "nucleic acid" as used herein refers to a polymer of ribonucleosides or deoxyribonucleosides comprising phosphodiester linkages between nucleotides subunits. Nucleic acids include, but are not limited to, genomic DNA, cDNA, hnRNA, mRNA, rRNA, tRNA, microRNA, fragmented nucleic acid, nucleic acid obtained from exosomes or from subcellular organelles such as mitochondria, and nucleic acid obtained from microorganisms or viruses that may be present on or in a sample. The nucleic acid can be double-stranded or single-stranded, linear or circular.

The term "short-chain nucleic acids" as used herein refers to a polymer of ribonucleosides or deoxyribonucleosides comprising less than <250 nt, preferably <200 nt or even <150 nt. In one of its particularly favorable aspects, the present invention aims to provide a solid basis for detection of cancer-related mutations in liquid biopsies like blood and plasma from cancer patients. Recent findings report that most cell-free DNA fragments circulating in cancer patients' blood measure between 180 and 200 bp. It should be noted that this size correlates with the regular size of DNA wrapped around a nucleosomes and released from cells upon apoptosis, which also suggests that cfDNA enters the blood through passive release from the massively dying cancer cells (cf. e.g. Jahr et al., Cancer Research 2001; Diaz and Bardelli, J. of Clin. Onco., 2014; and Devonshire et al. Anal. Bioanal. 2014). In view of the fact that the isolation of such small fragments is both technically challenging and desirable for diagnostic reasons, for the purposes of the present invention the terms "short-chain nucleic acid" and "short-chain nucleic acid" are to be construed as relating to nucleic acids of size below the above specified 250 nt.

As used herein, the terms "extracellular nucleic acids" or "extracellular nucleic acid" is to be understood as nucleic acids that are not contained in cells and refers both to extracellular RNA as well as to extracellular DNA and mixtures thereof. Respective extracellular nucleic acids are also often referred to as cell-free nucleic acids, like cell-free DNA (cfDNA) or cell-free RNA (cfRNA). Hence, extracellular nucleic acids usually are present outside of a cell or outside of a plurality of interconnected cells. Examples of typical extracellular nucleic acids can be found in e.g. in a cell-free fraction (or portion) of a biological sample such as a body fluid or a sample derived from a body fluid such as e.g. blood plasma. Extracellular nucleic acids include but are not limited to mammalian extracellular nucleic acids such as e.g. extracellular tumor-associated or tumor-derived DNA and/or RNA, other disease-related extracellular DNA and/or RNA, epigenetically modified DNA, fetal DNA, and/or RNA, small interfering RNA such as e.g. miRNA and siRNA. Such mammalian extracellular nucleic acids can exist as mononucleosomes and oligonucleosomes, or can be bound to the surfaces of blood cells by proteins that harboring nucleic acid-binding properties. Further, extracellular nucleic acids also importantly include non-mammalian extracellular nucleic acids such as e.g. viral nucleic acids, pathogenic nucleic acids released into the extracellular nucleic acid population e.g. from prokaryotes (e.g. bacteria), viruses or fungi.

In many medical conditions and infectious processes, t detection of presence or change in levels of extracellular and/or short-chain nucleic acids is of interest for screening, diagnosis, prognosis, and surveillance of disease progression, identifying potential therapeutic targets, and for monitoring treatment response. Additionally, elevated fetal DNA/

RNA in maternal blood is being used to determine e.g. gender identity, assess chromosomal abnormalities, and monitor pregnancy-associated complications. Besides mammalian extracellular nucleic acids that derive from e.g. tumor cells or the fetus, samples comprising extracellular short-chain nucleic acids may also comprise other nucleic acids of interest that are not comprised in cells, for example pathogen nucleic acids such as viral or bacterial nucleic acids. The efficient isolation of viral or bacterial nucleic acids from samples such as in particular blood samples or samples derived from blood is also important for many diagnostic applications.

Further, as used herein the terms "sample or "biological sample" is intended to include a variety of biological sources that contain nucleic acid and/or cellular material. The nucleic acid and/or cellular material from cells being tested are to determine if one or more of particular markers is present. Samples included are samples from cultures of cells, eukaryotic microorganisms or diagnostic samples such as a body fluid, body fluid precipitate, lavage specimen, fine needle aspirate, biopsy sample, tissue sample, cancer cells, cells from a patient, cells from a tissue or in vitro cultured cells from an individual being tested and/or treated for disease or infection, or forensic samples. Non-limited examples of body fluid samples include whole blood, bone marrow, cerebral spinal fluid, peritoneal fluid, pleural fluid, lymph fluid, serum, plasma, urine, chyle, stool, ejaculate, sputum, nipple aspirate, saliva, swabs specimen, wash or lavage fluid and/or brush specimens. In a preferred embodiment of the present invention, the nucleic acid-containing starting material is selected from the group consisting of a whole blood sample, a serum sample or a plasma sample.

BRIEF DESCRIPTION OF THE DRAWINGS

With specific reference now to figures, it is stressed that the particulars shown are by way of example and for purposes of illustrative discussion of the different embodiments of the present invention only. They are presented for the purpose of providing what is believed to be the most useful description of the principles and conceptual aspects of the invention. In this regard no attempt is made to show details of the invention in more detail than is necessary for a fundamental understanding of the invention. The description serves to illustrate to those skilled in the art how several forms of the invention may be embodied in practice and the figures, as summarised below serve to support the description, wherein:

FIG. 6: shows RT-qPCR results for a fully automated detection of Ebola viral RNA,

DETAILED DESCRIPTION OF THE INVENTION

Figure 1:
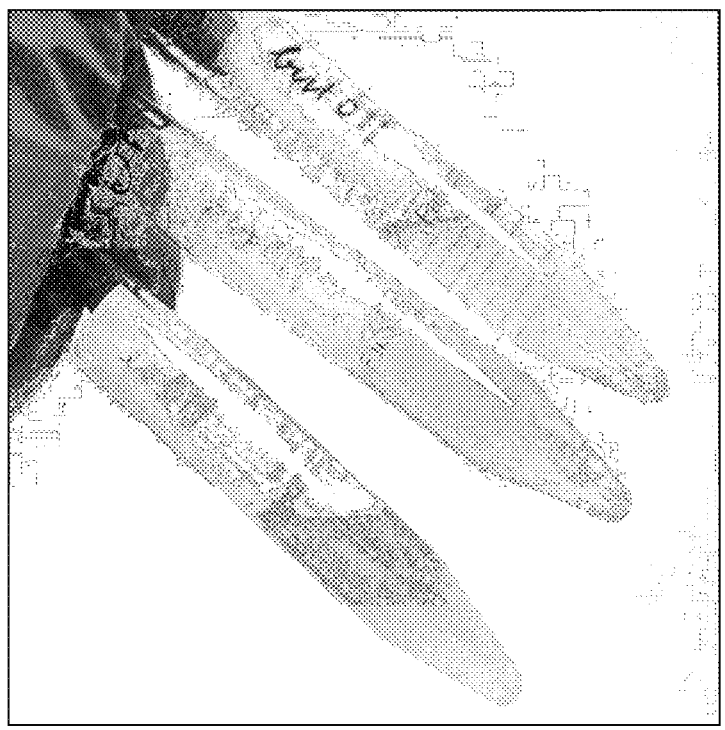
FIG. 1: shows the differences in protein precipitation levels depending on the type of alcohol admixed with a biological sample and a chaotropic agent present at high molarity.

The present invention concerns a method for isolation and/or purification of nucleic acids from a nucleic acid-containing starting material, the method comprising the steps of:
(a) binding the nucleic acids to a nucleic acid binding support material by contacting the nucleic acid-containing starting material with the nucleic acid binding support in the presence of at least one chaotropic compound and at least one alcohol; and
(b) optionally eluting the bound nucleic acids from the nucleic acid binding support material with an elution solution, such as pure water or an elution buffer e.g. TE buffer;

the method characterized in that
(i) the alcohol is an alcohol having 4 or 5 carbon atoms and is present in step a) in a concentration between 17% (v/v) and 60% (v/v), and in that
(ii) the at least one chaotropic compound is present in step a) in a concentration between 1.5 M and 5 M.

Alcohols having 4 or 5 carbon atoms, in particular the monohydroxy ones like butanols and pentanols, have limited solubility with water naturally present in biological samples, and separate from it forming a two-phase system. For this reason, these alcohols are not as frequently used in nucleic acid isolation procedures as much more popular and well mixing with aqueous environments ethanol and isopropanol. In view of the above, the present invention is based on two unexpected observations: firstly, that the two-phase system naturally forming between 50% water and 50% butanol or pentanol mixture, merges into a stable and uniform single phase solution (under STP[1]) when a chaotropic compound is added to said mixture to a molarity of roughly 1.5 M or higher. Secondly, it was observed that under the above-described conditions, butanols or pentanols not only allow binding of nucleic acids to silica, but also provide sufficiently hydrophobic conditions to prevent (or at least substantially slow down) proteins present in biological samples from immediate aggregation and precipitation.

[1] Standard temperature and pressure conditions

The present invention provides practically protein precipitation-free nucleic acid extraction conditions that at the same time allow nucleic acid to bind to the conventional nucleic acid binding materials. Firstly, this eliminates the need of performing a time-consuming proteolytic pre-digestion of samples, which would otherwise suffer from extensive precipitation that blocks the nucleic acid-binding surfaces. Secondly, thanks to the thus achieved acceleration and simplification of the procedure, the present method can also be easily automated. As a consequence, in a particularly preferred embodiment, the method of the invention can be performed without adding any protease to the step a), or without performing any incubations with a protease directly before subjecting the nucleic acid-containing starting material to the step a).

Typically, the binding of the nucleic acid in the present method of the invention is performed by silica adsorption. Therefore, in common embodiments, the nucleic acid binding support material will comprise silica, preferably selected from any of the following siliceous materials: silica gel, silicon dioxide, glass, zeolite, kaolin, silica gel, ceramics, silica membranes or resins (like in a column), and magnetic particles having a silica or glass surface. The binding support material can be of any form known in the art, including particles, microparticles, gel, fibers, beads, membranes, columns, and other supports such as test tubes and microwells, but preferably will be a membrane or a column.

In a typical embodiment, the method according to the present invention will usually further comprise at least one, possibly more, washing steps between steps a) and b). As will be appreciated by any skilled person, such washing steps of immobilized nucleic acids are well known in the art and conventionally employ ethanol solutions of different strengths, usually 50%, 70% or 75%, although other washing solutions or buffers can also be used.

The nucleic acids bound to the nucleic acid binding support according to the invention may then be processed or analyzed further in any known in the art manner. For example, depending on the planned subsequent steps, it possible to use the nucleic acids bound to the support material without elution. For this reason, step b) of the present method is described as optional.

In preferred embodiments of the provided herein method, the alcohol having 4 or 5 carbon atoms is a monohydroxy alcohol, i.e. butanol or pentanol including any isoform thereof. Therefore alcohol having 4 or 5 carbon atoms is preferably selected from the group consisting of n-butanol, sec-butanol, isobutanol, tert-butanol, 1-pentanol, 2-pentanol, 3-pentanol, 2-metyl 1-butanol, 3-metyl 1-butanol, 2,2-dimethyl 1-propanol, 2-metyl 2-butanol, 3-metyl 2-butanol, or a mixture thereof. Some of these butanol and propanol isoforms were observed to perform particularly well; hence, more preferably, the alcohol having 4 or 5 carbon atoms is selected from the group consisting of n-butanol, 1-pentanol, sec-butanol, isobutanol, tert-butanol, or a mixture thereof. Most preferably, the alcohol having 4 or 5 carbon atoms will likely be n-butanol.

In preferred embodiments, the concentration of the alcohol having 4 or 5 carbon atoms in step a) is comprised between 20% (v/v) and 55% (v/v), preferably between 25% (v/v) and 50% (v/v), more preferably between 30% (v/v) and 45% (v/v), most preferably between 35% (v/v) and 40% (v/v).

In further preferred aspects, the at least one chaotropic compound is a strong chaotropic compound, i.e. comprising any of the strongly chaotropic anionic groups such as $SCN^-$, $NCS^-$, $NO_3^-$, $ClO_4^-$, or $Cl_3CCOO^-$; and/or comprising any of the strongly chaotropic kationic groups such as guanidinium. Preferably, the chaotropic compound is selected from thiocyanates, isocyanates, perchlorates, or mixtures thereof. Most preferably, it will be guanidinium thiocyanate or guanidinium isothiocyanate. Alternatively however, it can also be a weaker chaotrope, e.g. sodium iodide, sodium perchlorate guanidinium hydrochloride, lithium acetate etc; provided at a higher concentration.

In preferred embodiments, the concentration of the chaotropic compound in step a) of the method of the invention is comprised between 2 M and 4.5 M, in some embodiments preferably between 2.5 M and 4 M, or more preferably between 3 M and 3.5 M.

Due to its ability to provide conditions for efficient isolation of nucleic acids that are shorter than <250 bp, the method of the invention also provides an efficient way of isolating/purifying cell-free circulating nucleic acids, such as double- or single-stranded DNAs or RNAs derived from apoptotic or necrotic cells or purposely excreted by various cell types during intracellular signalization. Such short-chain DNAs or RNAs can e.g. be detected in liquid biopsies and indicate a physiological or pathological state, such as pregnancy, an ongoing e.g. viral infection, inflammation, or cancer. Thus, in a preferred embodiment, the present method is employed for the isolation and/or purification of short-chain nucleic acids, herein defied as having a length of less than 250 nt (<250 nt), preferably of about the size of or less than 200 nt.

Along these lines, in preferred embodiments, the nucleic acid-containing starting material subjected to the method of the invention is a biological sample, preferably a liquid biological sample selected from the group consisting of whole blood, serum, plasma, cerebrospinal fluid (CSF), urine, tears, saliva, sweat, vomit, feces, sperm, or buffy coat. All of the above can easily be used to screen for the presence/type of extracellular nucleic acids either present in the cell-free matrix of such samples, or in the intracellular matrix present between cells suspended in said matrix, or on surfaces of such cells. In most preferred embodiments, the material is selected from the group consisting of whole blood, serum, plasma, cerebrospinal fluid (CSF), and urine.

It should be noted however, that in possible embodiments, the present method also allows to isolate intracellular nucleic acids, such as genomic DNA, different cellular RNA types, small RNAs like microRNAs in particular, as well as nucleic acids of intracellular pathogens like viruses or protozoa e.g. *Plasmodium*. In such embodiments, the nucleic acid-containing starting material subjected to the method of the invention can be any source of cells such as a tissue sample, a cell pellet, and preferably is a suspension of cells in any liquid, such as PBS or other buffer.

In further preferred embodiments, the present method can also be employed for the detection of pathogenic viral nucleic acids, in particular the ones present in mammalian bodily fluids, either in their cell-free fraction or still inside their host cells. Examples of pathogenic viruses that can be detected following nucleic acid isolation/purification performed according to the present method are negative-stranded RNA enveloped viruses such as the Ebola virus. Therefore, in a possible embodiment, the nucleic acid-containing starting material is whole blood and the present method is performed to isolate and/or purify RNA of Ebola virus.

In a particular aspect of the invention, step a), more preferably both steps a) and b) of the present method are performed at a temperature of ≥4° C. and ≤40° C., preferably ≥15° C. and ≤25° C. In essence, the reaction is not particularly temperature sensitive, thus providing a further advantage over art known isolation procedures. This allows the method to be carried out at normal room temperature, without the presence of any specialized temperature-regulating system, even in tropical areas.

Therefore, the present method not only has the advantages of being robust and performable at room-range temperatures (about 20° C.), but it is also easily adaptable for full automation. Thus, in an advantageous embodiment requiring minimal handling and no advanced laboratory skills, the method of the invention is performed on an automated system. Suitable automated systems are well known in art and include e.g. the Biocartis NV platform Idylla. Thus, in a further advantageous embodiment, a method is provided wherein steps a) and b) are preferably performed on a cartridge that is engageable with and removable from such automated system. An example of such cartridge can be found in EP1904234.

Along these lines, in a further aspect, the present invention provides an automated diagnostic method for detecting nucleic acids on an automated system, the method comprising the steps of:

a) providing a nucleic acid-containing starting material into an automated system;
b) isolating and/or purifying nucleic acids in said automated system, according to the isolation and/or purification method in accordance with the above embodiments;
(c) performing amplification in said automated system of target nucleic acids isolated and/or purified in step (b); and
(d) detecting the target nucleic acids amplified in step (c), preferably also on said automated system.

In preferred embodiments, the amplification in step (c) will be performed using PCR. However, it can also be performed using an alternative nucleic acid amplification method such as the more recent isothermal approaches including transcription-mediated amplification (TMA), loop mediated amplification, nucleic acid sequence based amplification, strand displacement amplification, or multiple displacement amplification. Alternatively, step (c) instead of involving amplification of target nucleic acids, may involve generation of signals from said target nucleic acids isolated and/or purified in step (b) and amplifying said signals according to any known in the art technique. In such instance, the following step (d) would involve detecting the signals amplified in step (c), preferably also on said automated system. An example of such signal-amplification technique compatible with the afore-mentioned embodiment of the method according to the invention is branched DNA assay (bDNA) that can be used e.g. for assessing viral load in a sample.

In particularly preferred embodiments of said automated diagnostic method, no incubation with a protease is performed between the steps a) and b) or during the step b).

In a preferred embodiment, the PCR performed in step c) of the present automated diagnostic method is a quantitative PCR (qPCR).

In another preferred embodiment, compatible with the above embodiments, an automated diagnostic method is provided wherein at least the steps (b) and (c) are performed on a cartridge engageable with and removable from the automated system.

In one embodiment, the present automated diagnostic method allows to detect extracellular nucleic acids such as viral nucleic acids or tumor-derived or fetal circulating DNA.

In line with the latter example, in a second preferred embodiment, the automated diagnostic method also allows for detection of short-chain nucleic acids having a length of <250 nt, preferably equal to or smaller than about 200 nt, such as micro RNAs, or short double stranded (ds)DNA fragments such as the afore-mentioned tumor-derived or fetal circulating DNA.

In an alternative embodiment, the automated diagnostic method of the invention allows to detect viral nucleic acids potentially present in both the cellular as well as in the extracellular fractions of the nucleic acid-containing starting material. In a particularly preferred embodiment of said automated diagnostic method, the detected nucleic acid is a nucleic acid of Ebola virus. In an advantageous embodiment, the nucleic acid of Ebola virus is Ebola RNA. In such embodiment, the PCR performed in step c) is preferably a reverse transcriptase PCR (RT-PCR), most preferably a quantitative reverse transcriptase PCR (qRT-PCR). In such instance, the nucleic acid-containing starting material will most preferably be whole blood; however, it can also be another bodily fluid such as vomit, feces, urine, sweat, sperm etc.

Chaotropic salts like GuSCN do not dissolve in butanols or pentanols. Therefore, to achieve the nucleic acid isolation/purification conditions of the present invention, the chaotropic compound can directly be dissolved in a liquid sample like plasma, serum, or CSF, after which the appropriate alcohol of 4- or 5-carbon atoms can be added. More conveniently however, the isolation/purification conditions are created by mixing a biological sample with or suspending it in an aqueous extraction buffer comprising the chaotrope and the alcohol having 4 or 5 carbon atoms at a higher concentration.

Thus, in a further aspect, the present invention also provides an aqueous extraction buffer for isolation and/or purification of nucleic acids, said buffer comprising
(i) an alcohol having 4 or 5 carbon atoms, in a concentration between 20% (v/v) and 65% (v/v), preferably between 35% (v/v) and 60% (v/v), most preferably between 40% (v/v) and 50% (v/v) and
(ii) at least one chaotropic compound in a concentration between 3.3 M and 6.7 M, preferably between 3.5 M and 5.5 M, most preferably between 3.7 M and 4.5 M.

As this aqueous extraction buffer is to be used in the methods of the invention, the same preferred 4 or 5 carbon atom alcohols and chaotropes as mentioned apply also here. Thus, the alcohol having 4 or 5 carbon atom is preferably selected from the group consisting of n-butanol, 1-pentanol, sec-butanol, isobutanol, tert-butanol, or a mixture thereof, and most preferably is n-butanol. Similarly, the at least one chaotropic compound comprised in the present extraction buffer is preferably selected from thiocyanates, isocyanates, perchlorates, hydrochlorides, or mixtures thereof; and most preferably is guanidinium thiocyanate or guanidinium isothiocyanate.

In a next aspect, the present invention also provides a kit for isolation and/or purification of nucleic acids, preferably short-chain and/or extracellular, or viral nucleic acids, from a nucleic acid-containing starting material, the kit comprising at least the extraction buffer according to the invention. Such kit of the invention may also comprise typical additional elements as instructions for use of the kit, but advantageously will further comprise any or all of the following:
(a) a nucleic acid binding support material suitable for binding nucleic acids, such as a siliceous material;
(b) a wash solution such as a wash buffer;
(c) an elution solution such as an elution buffer.

In a preferred embodiment, the kit comprises a cartridge that is engageable with an automatic system of choice, wherein at least the extraction buffer of the invention is provided inside of the cartridge.

In further preferred embodiments, the cartridge further comprises a nucleic acid isolation and/or purification compartment comprising the nucleic acid binding support material, wherein said nucleic acid isolation and/or purification compartment houses or holds said extraction buffer or is in fluid communication with another cartridge compartment housing said extraction buffer. Preferably, such cartridge further comprises additional compartments in fluid communication with the nucleic acid isolation and/or purification compartment, said additional compartments comprising for example the wash solutions or elution solutions etc.

Finally, in another aspect, the present invention provides a use of the isolation/purification method of the invention, the afore-described extraction buffer, and the kit in any of the following:

isolation and/or purification of extracellular nucleic acids, such as among others nucleic acids from pathogens like viruses, from exosomes, as well as fetal or tumor-derived nucleic acids;

isolation and/or purification of short-chain nucleic acids having a length of <250 nt, most preferably equal to or smaller than about 200 nt;

isolation and/or purification of viral nucleic acids, such as Ebola RNA;

diagnosis of infections (e.g. viral, bacteriological, fungal, or protozoan), pathological (e.g. cancer), or physiological (e.g. pregnancy) conditions.

Further fields of application, however, can be found outside the area of diagnostics, for example in forensics or other fields in which the purification of short-chain nucleic acids is crucial In a preferred embodiment, the above-listed uses are applied on a nucleic acid-containing starting material that is selected from a liquid biopsy sample, such as a whole blood sample, a serum sample, a plasma sample, a CSF sample; or on a different type of a biological liquid sample such as a urine sample.

In line with the above, it is within a particular aspect of the present invention, that the present nucleic acid isolation/purification method, the extraction buffer, and the kit are used in an automatic system, for example a cartridge system.

EXAMPLES

The present invention is based on the unexpected finding that alcohols that are more hydrophobic than ethanol and isopropanol and that usually do not mix with water, are particularly suitable for performing silica adsorption-based nucleic acid extraction in the presence of a chaotropic agent at a molarity higher than at least 1.5 M.

It has already been known from the Boom protocol, that binding of nucleic acids to silica is favored in the presence of alcohols like as ethanol or isopropanol. However, both of these alcohols when present at the required concentration cause immediate aggregation of proteins, leading to irreversible clogging of silica membranes and nonspecific trapping of nucleic acids. As a consequence, in a typical Boom protocol, an extensive protease digestion is required to sufficiently reduce the peptide length and thus prevent this impediment.

The present invention circumvents the necessity of a protease-treatment step by providing a method for nucleic acid isolation and/or purification from a protein- and nucleic acid-containing starting material, wherein said protein- and nucleic acid-containing starting material is contacted with a nucleic acid binding support material in the presence of at least one chaotropic compound in a concentration between 1.5 M and 5 M and at least one alcohol having 4 or 5 carbon atoms in a concentration between 17% (v/v) and 60% (v/v).

The role of the chaotropic agent within this range of molarity is to first, provide for mixing of the 4 or 5 carbon atom alcohol with water (either added or present in the nucleic acid-containing starting material, for example a biological sample) and, secondly, to provide for sufficient chaotropic action to denature the proteins present in the nucleic acid-containing starting material and thus to some extent render them inactive. The latter is particularly important if the isolated nucleic acid is RNA, which would be immediately targeted and digested by copious amount of RNAses in most biological samples.

On the other hand, the role of the alcohol having 4 or 5 carbon atoms, preferably being butanol or pentanol, is to, firstly, provide conditions enabling nucleic acid binding to the support material (usually silica); and, secondly, to in the meantime keep the denaturing proteins sufficiently soluble in order not to interfere with efficient binding of the nucleic acids to the support. Therefore, the selective use of butanols and/or pentanols in the given nucleic acid isolation conditions substantially reduces protein precipitation thus making a pre-treatment with protease redundant.

The above-described ability is well demonstrated in FIG. 1 showing a plasma sample mixed with a high amount of guanidinium thiocyanate (GuSCN) and divided in three replicates of 1 ml each of which was then two times diluted with respective alcohol selected from (1) ethanol (labeled "etOH"), (2) isopropanol (labeled "propOH"), and (3) butanol (labeled "butOH"). Following the addition of respective alcohols to the final concentration of 50%, the final GuSCN concentration in these replicates was about 2 M. As can be appreciated from FIG. 1, the plasma-GuSCN solutions mixed with either ethanol or isopropanol became visibly cloudy due to almost immediate and heavy protein precipitation at room temperature. Conversely, as demonstrated by a readily visible scale on the tube containing the sample, no precipitates formed in the plasma-GuSCN mixture with butanol. The latter generally held true for other tested within the above specified concentration range GuSCN and butanol or pentanol mixes with water and plasma or whole blood including e.g. 2.9M GuSCN and 50% n-butanol, 2.9M and 51% tert-butanol, 3.7M GuSCN and 32% 1-pentanol, 3.2M GuSCN and 38% 1-pentanol, 2.9M GuSCN and 46% 3-pentanol. The type of precipitates, if visible, that formed in these solutions naturally depended on how protein-dense was the tested biological sample (e.g. whole blood is a more challenging material than plasma). In general however, they were transparent and sometimes could only be seen following centrifugation.

Figure 2:
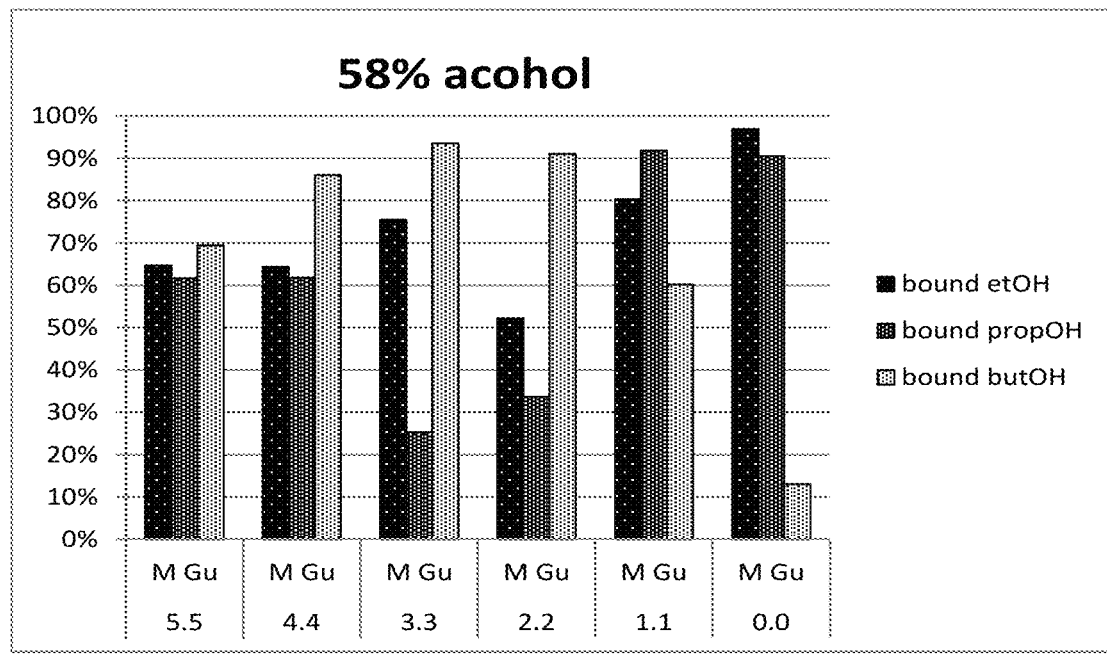
FIG. 2: shows differences of DNA-binding properties to a siliceous binding material as a function of chaotropic salt concentration and depending on the alcohol type.

The next step was to compare the ability of nucleic acids present in plasma samples treated with different concentrations of a chaotropic agent to bind to a siliceous support material in the presence of ethanol, isopropanol or butanol. To do so, several plasma samples were first pooled, divided into repeats containing 58% of one of the three alcohols and GuSCN at different concentrations selected from 1.1M, 2.2M, 3.3M, 4.4M and 5.5M. One plasma and 58% alcohol of choice sample for each alcohol was kept as a binding control with no GuSCN added (sample "0.0"). Then, each of said prepared plasma/GuSCN/alcohol mixes was spiked and vortexed with small oligos of 50 and 150 bp labelled with different fluorescent dyes (Texas Red and Atto647N). Fluorescence values of each mixture were measured, after which all the mixtures were subjected to nucleic acid isolation on silica columns. The silica-adsorbed nucleic acids were then eluted in TE buffer, followed by a second fluorescence measurement in the flow-through. FIG. 2 shows the relative fluorescence values of the second measurement to the first measurement (y axis) in the tested samples (x axis), as normalised to TE. The results show that no chaotropic agent is in fact needed for the DNA to pass through a silica membrane for as long as at least 50% ethanol or propanol is present. For these alcohols, strong precipitation was observed at all GuSCN concentrations and the DNA yield was the highest at no GuSCN or at 1.1M GuSCN where the precipitation was the lowest. For butanol on the other hand, two separate liquid phases were observed at no GuSCN and still at 1.1M GuSCN, which could explain the poorer extraction efficiencies on the column. However, at GuSCN concentrations of 2.2M and higher the plasma-butanol mixture was a uniform and clear solution and resulted in the DNA extraction rates much better as compared to corresponding ethanol or isopropanol mixtures. The latter can likely be explained due to stronger protein precipitation at higher GuSCN concentrations in ethanol and isopropanol samples, which likely causes trapping of nucleic acids in protein complexes and blocking of the silica membrane. In contrast, no protein precipitation was observed in butanol-treated plasma at least till GuSCN concentration of 4.4M.

Figure 3:
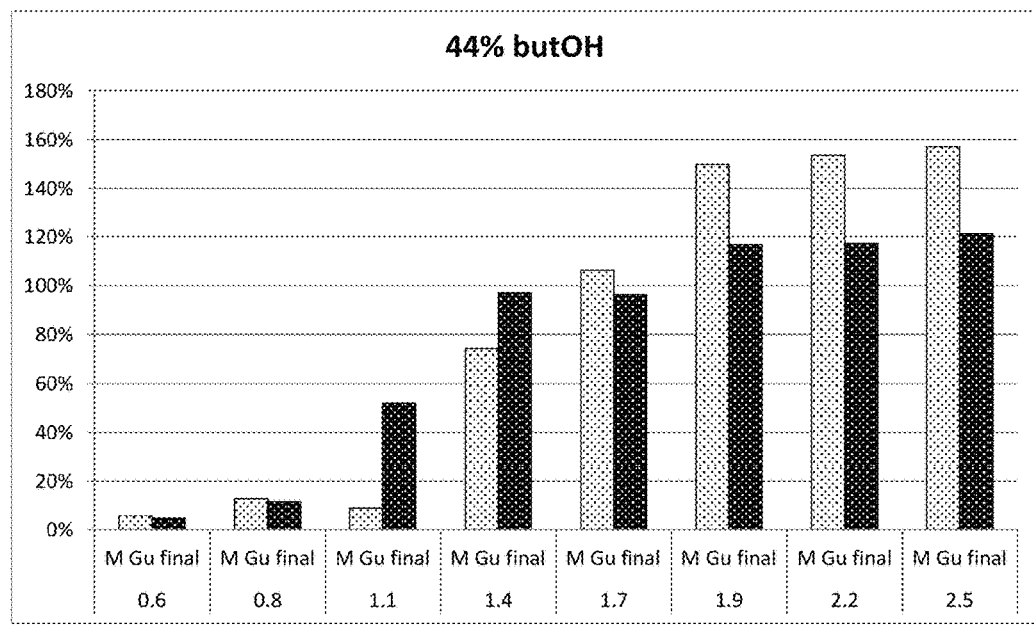
FIG. 3: shows extraction rates of short DNA fragments of 50 bp (light bars) and 150 bp (dark bars) in the presence of 44% n-butanol as a function of GuSCN concentration.

In order to determine the efficiency of short-chain DNA binding to silica membrane as a function of the chaotropic agent concentration, eight plasma and 44% n-butanol samples containing different concentrations of GuSCN (from 0.6 M to 2.5 M) were prepared as described above and spiked with small amounts of the two differently labelled oligos of 50 bp (labelled with Texas Red) and 150 bp (labelled with Atto647N) in size. The samples were directly (i.e. without protease treatment) loaded on silica columns, after which the bound nucleic acids were eluted with 500 ul TE. To discern between the recovered 50 bp and 150 bp oligo fragments in the flow-through, the samples were resolved by size using agarose gel electrophoresis. Fluorescence was measured for each fragment at its appropriate emission wavelength and expressed as relative fluorescence results by normalizing against the input fluorescence in TE for both of the fragments as shown in FIG. 3, wherein the lighter bars show the recovery of the shorter 50 bp fragment and the darker bars of the slightly longer 150 bp fragment. Values higher than 100% are sometimes observed and are merely a consequence of the normalizations and the experimental variability on both these fluorescence measurements. However, trends can clearly be seen: the results show that with increasing concentrations of the chaotropic agent, the amount bound of the shorter 50 bp fragment and the 150 bp fragment increase. Similar finding was observed for increasing alcohol concentrations, which also was favourable for the preferential isolation of shorter fragments (data not shown).

The above-described isolation of the short (50 bp and 150 bp) oligo fragments spiked to plasma shows that the method the invention not only allows for effective retrieval of even very short-chain nucleic acids from a complex biological sample, but also that it allows to eliminate the protease treatment, which in the state-of-the-art protocols is required to avoid clogging or otherwise blocking of the nucleic-acid binding support. The latter thus confers a major advantage over the known ethanol or isopropanol-based nucleic acid extractions, wherein the time-consuming protease digestion (often of about 1 hr) at elevated temperatures is absolutely necessary. As a result, the nucleic acid isolation and/or purification method according to the invention, as well as the provided herein extraction buffers and kits, can also be used for fully automated DNA or RNA extractions on automated systems, for example cartridge-based systems.

Figure 4:
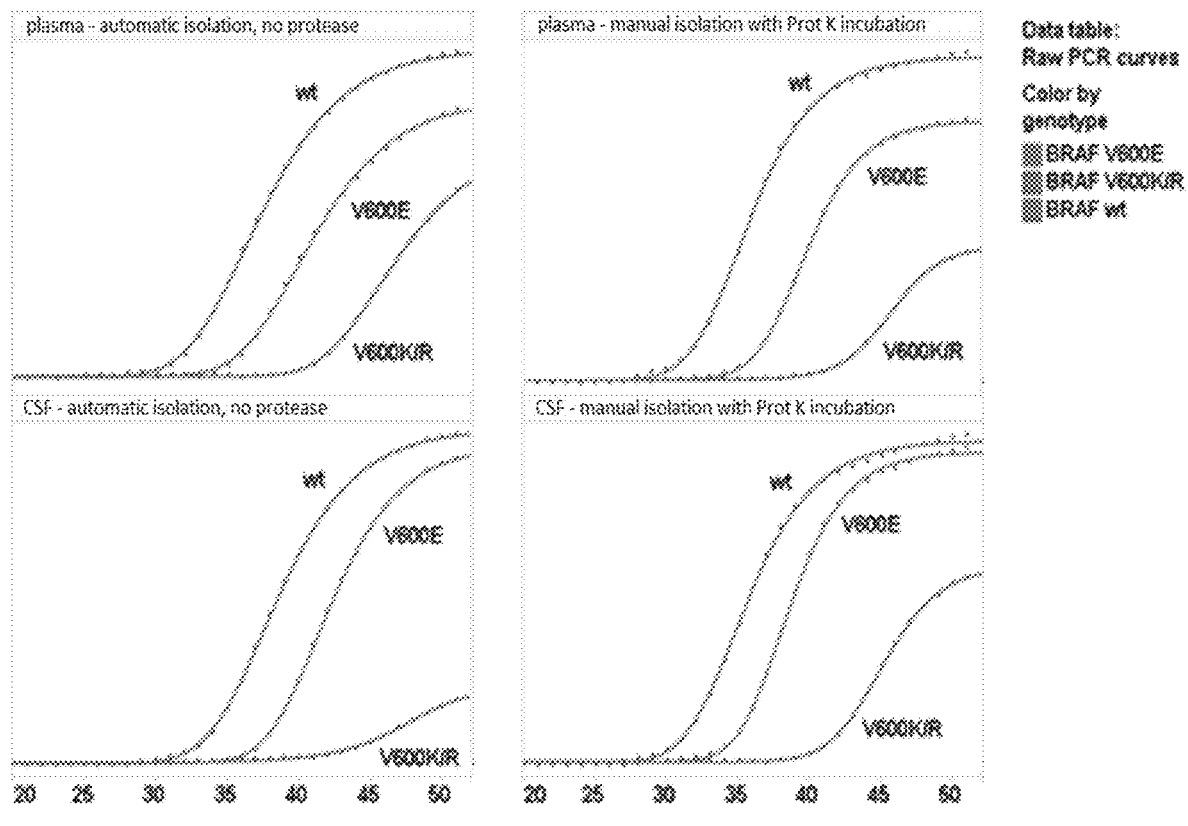
FIG. 4: shows the results of a BRAF mutation analysis performed on extracellular nucleic acids isolated from plasma or CSF clinical samples using a fully automated nucleic acid extraction protocol without protease treatment.

To test the above, aqueous extraction buffer comprising 44% n-butanol and 3.7M GuSCN were included inside of a Biocartis Idylla BRAF Mutation Test microfluidic cartridge in place of the standard lysis buffer currently present in the commercially available Idylla BRAF Mutation Test cartridges. 1 ml of plasma and 1 ml of CSF obtained from melanoma patients with confirmed BRAF V600E mutations were provided into the sample-accepting compartments of two such modified Idylla BRAF Mutation Test cartridges, respectively, after which the cartridges were closed and fed into Idylla automated platform, after which all the subsequent steps were performed automatically. In particular, both of the BRAF Test cartridges were configured to admix 5.5 ml of the 44% n-butanol and 3.7M GuSCN extraction buffer with the respective clinical sample during the sample lysis and nucleic extraction step. The membrane bound nucleic acids were washed with a wash buffer comprising 90% ethanol and eluted from the membrane with 1×PCR buffer (50 mM KCl, 3 mM MgCl2, 10 mM Tris pH 8.6 @ 25° C.) and subjected to a multiplex qPCR designed to detect wt BRAF, BRAF V600E, and BRAF V600K/R. In parallel, to assess the efficiency of the above-described automated nucleic acid extraction of the tumor-derived circulating DNA on the Idylla cartridge, nucleic acids from the same samples were also extracted using an efficient commercially available GuSCN and isopropanol-based nucleic acid extraction kit. The extraction was manually performed on a column according to the manufacturer's instructions including Proteinase K incubation for 1 hr at 60° C., due to the fact that: (i) the volumes used in said protocol exceed the capacity of the cartridge, and also because (ii) without the Proteinase K digestion, the extraction cannot proceed due to extensive precipitation causing column or membrane clogging. Following the manual extraction, the nucleic acids purified from plasma and CSF were directly loaded onto BRAF Mutation Test cartridges and analyzed via qPCR as described above. The results of both extraction strategies performed on plasma and CFS samples are shown in FIG. 4. Both the fully automated analysis on cartridge and the semi-automated (manual bench-top extraction followed by qPCR analysis on cartridge) protocols yielded comparable results and succeeded in detecting the BRAF V600E mutation both in plasma as well as in CSF.

The above results demonstrate the suitability of the method of the invention for the isolation of very short and extracellular DNA from human samples, using the silica adsorption principle without the need of pretreating said samples with a protease. Elimination of the protease treatment, which is usually performed at elevated temperatures, is particularly desirable for protocols aiming at isolating and/or purifying RNA, which is much more vulnerable to degradation as compared to DNA. Therefore, the method of the invention has also been tested for isolating and detecting single stranded RNA of Ebola virus in human whole blood samples.

Figure 5:
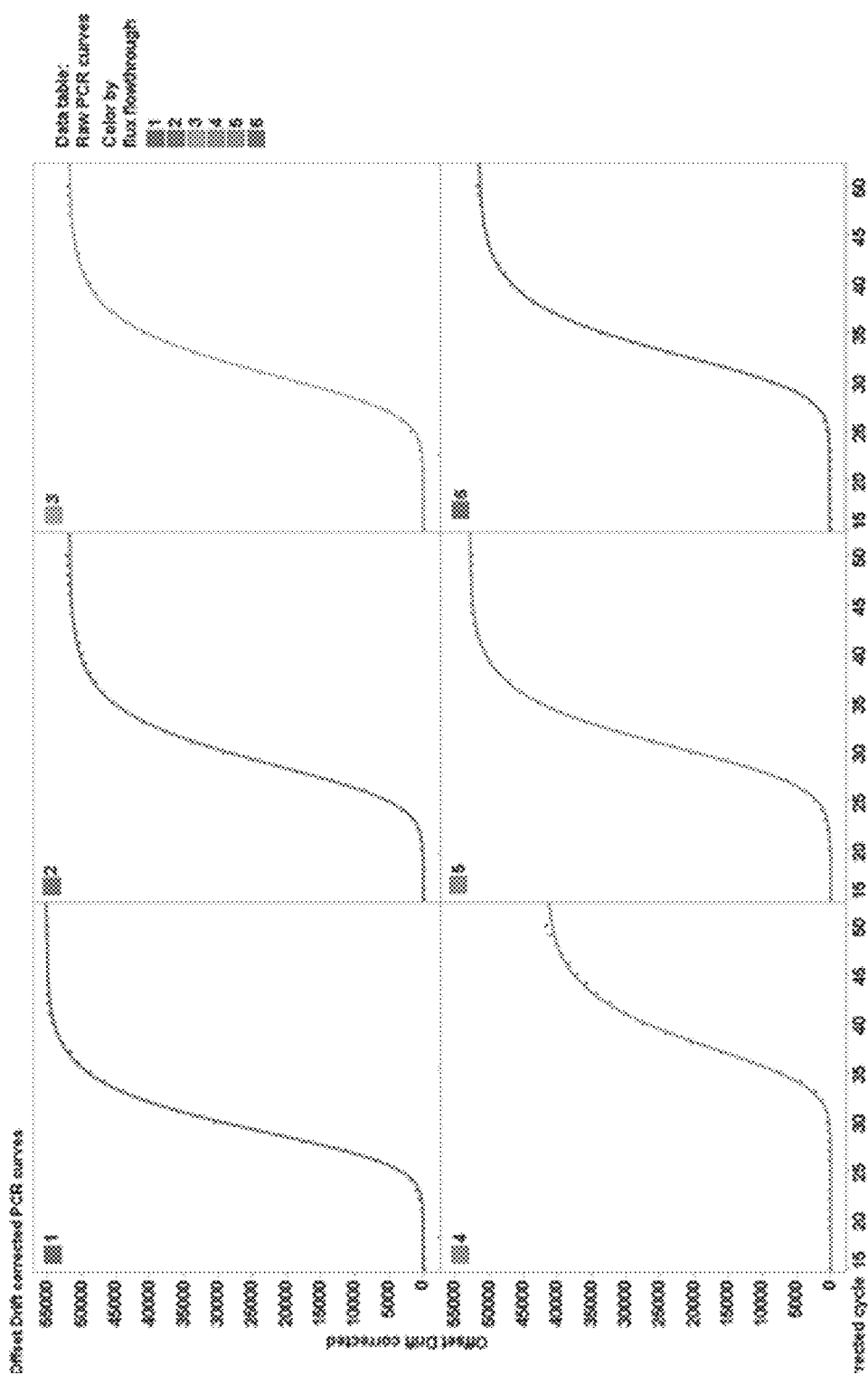
FIG. 5: shows performance of different alcohols during extraction and analysis of a viral RNA from whole blood samples.

To do so, as a first step, different extraction buffers comprising different 4 or 5 carbon atom-containing alcohols and different concentrations of GuSCN were tested. It should be noted that blood as a starting material is extremely complex due to being rich in protein content and also various complexes, such as heme groups. In addition, blood is rich in RNAses, which determines the extraction buffer should preferably have high concentration of the chaotrope to provide for quick protein denaturation in order to protect the viral RNA of interest. Different alcohol-GuSCN solutions tested included (1) 57% n-butanol and 3.3M GuSCN; (2) 37% 1-pentanol and 4.2M GuSCN; (3) 43% 1-pentanol and 3.7M GuSCN; (4) 56% 3-methyl-1-butanol (isoamyl alcohol) and 2.8M GuSCN; (5) 58% tert-butanol and 3.3M GuSCN; and (6) 53% 3-pentanol and 3.5M GuSCN. First, 1.5 ml of each of said extraction buffers was mixed with 200 ul of a human blood sample, after which the extraction-buffer/blood mixes were loaded on silica spin columns with a vacuum setup in order to time the flux of corresponding mixes through the columns' length. In contrast to previously tested ethanol or isopropanol and GuSCN mixes, and with the exception of the isoamyl alcohol-containing mix, column clogging did not occur. Concerning the isoamyl alcohol-containing mix, where clogging did occur to certain extent, it should be noted that it was the mix comprising the lowest GuSCN concentration. Then, nucleic acids bound on the columns were eluted with RNAse free water, after which they were subjected to reverse transcriptase quantitative PCR (RT-qPCR) with Ebola-specific primers and probes. Raw RT-qPCR curves for the above-listed nucleic-acid extraction conditions are shown in FIG. 5 and prove that the method of the invention is equally suitable for RNA isolation.

Figure 6:
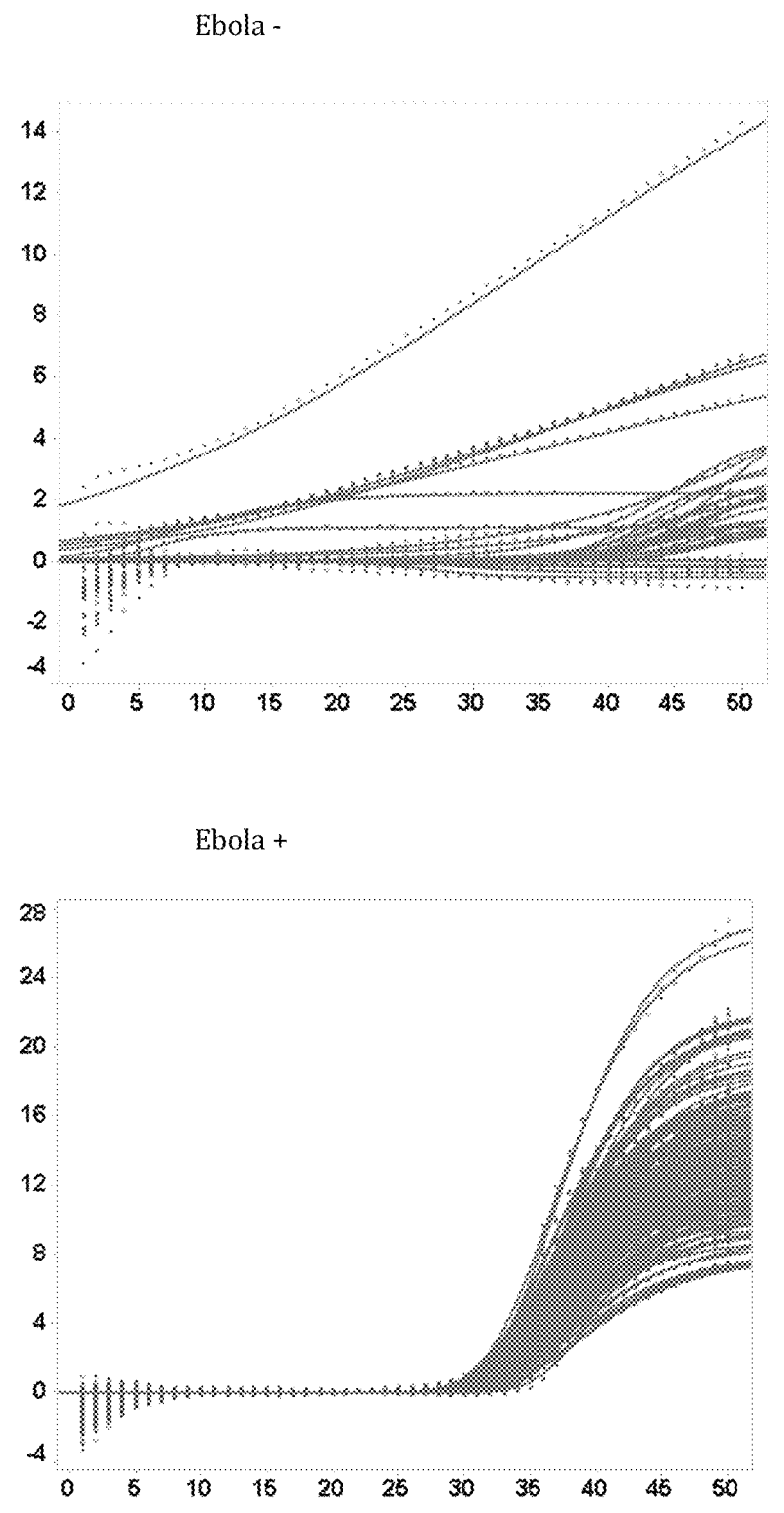

As a next step, the Ebola RNA isolation and detection protocol was tested in a fully automated setting on the Idylla platform. The protocol was designed to confine all the processing steps performed on a potentially infectious blood sample in a single disposable plastic cartridge. Firstly, about 200 ul of a whole blood sample to be tested is fed into the cartridge, after which the cartridge is closed loaded onto the Idylla instrument. Therein, inside of the cartridge, the sample is mixed with an excess of an aqueous extraction buffer containing 4M GuSCN and 22% butOH. Under these conditions, the sample components including the potentially comprised therein viral particles are lysed, and the nucleic acids are adsorbed onto a silica extraction membrane. Excess cell debris and proteins are subsequently washed from the silica membrane and then the nucleic acids are eluted using RNAse free water. Subsequently, the thus purified RNA is reverse-transcribed into cDNA while still within the cartridge, which then is subjected to a qPCR using Ebola-specific primers and probes. Results obtained from a the above described protocol are shown in FIG. 6, wherein the panel on the left shows raw qPCR curves obtained for Ebola-negative samples, whereas the panel on the right shows the curves for Ebola-positive controls.

The invention claimed is:

1. A method for isolating and/or purifying nucleic acids from a nucleic acid-containing starting material, the method comprising: step (a) binding the nucleic acids to a nucleic acid binding support material by contacting the nucleic acid-containing starting material with the nucleic acid binding support in the presence of at least one chaotropic compound and at least one alcohol, wherein:
   (i) the alcohol is an alcohol having 4 or 5 carbon atoms and is present at a concentration between about 17% (v/v) and about 50% (v/v), and in that
   (ii) the at least one chaotropic compound is present at a concentration between about 1.5 M and about 4.5 M.

2. The method of claim 1 further comprising: step (b) eluting the bound nucleic acids from the nucleic acid binding support material with an elution buffer.

3. The method according to claim 1, wherein no protease is added to step (a) or no incubation with a protease is performed directly before subjecting the nucleic acid-containing starting material to step (a).

4. The method according to claim 1, wherein the alcohol having 4 or 5 carbon atoms is a monohydroxy alcohol.

5. The method according to claim 4, wherein the monohydroxy alcohol is selected from the group consisting of n-butanol, sec-butanol, isobutanol, tert-butanol, 1-pentanol, 2-pentanol, 3-pentanol, 2-methyl 1-butanol, 3-methyl 1-butanol, 2,2-dimethyl 1-propanol, 2- methyl 2-butanol, 3-methyl 2-butanol, or a mixture thereof.

6. The method according to claim 4, wherein the monohydroxy alcohol is selected from the group consisting of n-butanol, 1-pentanol, sec-butanol, isobutanol, tert-butanol, or a mixture thereof.

7. The method according to claim 1, wherein the alcohol having 4 or 5 carbon atoms is present in step (a) at a concentration between about 20% (v/v) and about 50% (v/v).

8. The method according to claim 1, wherein the alcohol having 4 or 5 carbon atoms is present in step (a) at a concentration between about 35% (v/v) and about 40% (v/v).

9. The method according to claim 1, wherein the at least one chaotropic compound is selected from thiocyanates, isocyanates, perchlorates, hydrochlorides, or mixtures thereof.

10. The method according to claim 1, wherein the at least one chaotropic compound is guanidinium thiocyanate.

11. The method according to claim 1, wherein the at least one chaotropic compound is present in step (a) at a concentration between about 2 M and about 4.5 M.

12. The method according to claim 1, wherein the at least one chaotropic compound is present in step (a) at a concentration between about 3 M and about 3.5 M.

13. The method according to claim 1, wherein the nucleic acid-containing starting material is a liquid biological sample selected from the group consisting of whole blood, serum, plasma, cerebrospinal fluid (CSF), and urine.

14. The method according to claim 1, wherein said method is performed on an automated system on a removable cartridge.

15. An automated diagnostic method for detecting target nucleic acids, the method comprising the steps of:
   (a) providing a nucleic acid-containing starting material into an automated system;
   (b) isolating and/or purifying nucleic acids in said automated system, according to the method of claim 1;
   (c) performing amplification in said automated system of target nucleic acids isolated and/or purified in step (b); and
   (d) detecting the target nucleic acids amplified in step (c).

16. The automated diagnostic method according to claim 15, wherein at least the steps (b) and (c) are performed on a cartridge.

* * * * *